United States Patent
Leonard et al.

(10) Patent No.: US 8,185,319 B2
(45) Date of Patent: *May 22, 2012

(54) METHOD OF COMPENSATION OF DOSE-RESPONSE CURVE OF AN ASSAY FOR SENSITIVITY TO PERTURBING VARIABLES

(75) Inventors: Stephen W. Leonard, Unionville (CA); Samad Talebpour, Richmond Hill (CA)

(73) Assignee: Novx Systems Canada Inc., Richmond Hills, ON (CA)

( * ) Notice: Subject to any disclaimer, the term of this patent is extended or adjusted under 35 U.S.C. 154(b) by 1383 days.

This patent is subject to a terminal disclaimer.

(21) Appl. No.: 11/730,927

(22) Filed: Apr. 4, 2007

(65) Prior Publication Data

US 2007/0250271 A1   Oct. 25, 2007

Related U.S. Application Data

(63) Continuation-in-part of application No. 11/334,749, filed on Jan. 19, 2006.

(51) Int. Cl.
*G01N 33/48* (2006.01)
*G01N 33/50* (2006.01)

(52) U.S. Cl. ............................... 702/19; 702/20

(58) Field of Classification Search .................. None
See application file for complete search history.

(56) References Cited

U.S. PATENT DOCUMENTS

| | | | |
|---|---|---|---|
| 4,483,823 A | 11/1984 | Umetsu | |
| 4,933,146 A | 6/1990 | Meyer | |
| 5,387,503 A | 2/1995 | Selmer | |
| 5,648,274 A | 7/1997 | Chandler | |
| 5,919,642 A | 7/1999 | Khanna | |
| 6,514,770 B1 | 2/2003 | Sorin | |
| 7,016,787 B2 * | 3/2006 | Vaisberg et al. | 702/19 |
| 7,320,878 B2 * | 1/2008 | Gulnik et al. | 435/23 |
| 2004/0022677 A1 * | 2/2004 | Wohlstadter et al. | 422/52 |
| 2006/0199221 A1 * | 9/2006 | Talebpour | 435/7.1 |
| 2006/0199236 A1 | 9/2006 | Talebpour | |
| 2006/0210435 A1 * | 9/2006 | Alavie et al. | 422/65 |
| 2006/0263836 A1 * | 11/2006 | Connelly et al. | 435/7.92 |

OTHER PUBLICATIONS

De Lean et al., Simultaneous analysis of families of sigmoidal curves: application to bioassay, radioligand assay, and physiological dose-response curves, Journal of Physiology, 1978, 235 (2): E97-E102).*

* cited by examiner

*Primary Examiner* — Jason Sims
(74) *Attorney, Agent, or Firm* — Lynn C. Schumacher; Stephen W. Leonard; Hill & Schumacher

(57) ABSTRACT

Assays and methods of compensating for changes in a dose-response curve of an assay due to variations in a perturbing variable by firstly measuring the dose-response curve, the individual assay parameters, at different values of the perturbing variable. Next, unknown samples are assayed simultaneously with a known standard at a chosen analyte concentration with a value of the perturbing variable being unknown and the dose-response curve unknown. The different dose-response curves from the first step are used to determine a mathematical relationship between assay parameters and the assay signal of the known standard. The assay parameters that are valid for the unknown value of the perturbing variable can be obtained by substituting the value of the assay signal from the known standard into the mathematical relationship and solving for the assay parameters.

28 Claims, 7 Drawing Sheets

METHOD OF COMPENSATION OF DOSE-RESPONSE CURVE OF AN ASSAY FOR SENSITIVITY TO PERTURBING VARIABLES

CROSS REFERENCE TO RELATED U.S. APPLICATIONS

This patent application is a continuation-in-part (CIP) of U.S. Utility patent application Ser. No. 11/334,749 filed on Jan. 19, 2006, in English, entitled METHOD OF COMPENSATION OF DOSE-RESPONSE CURVE OF AN ASSAY FOR SENSITIVITY TO PERTURBING VARIABLES, and which is incorporated herein by reference in its entirety.

FIELD OF THE INVENTION

The present invention is related to assays and methods of compensating for changes in the dose-response curve of an assay where such changes are due to variations in a perturbing variable such as temperature.

BACKGROUND OF THE INVENTION

Assays of samples (i.e. biological, environmental etc) are routinely used to detect and measure the presence and the concentration of analytes such as drugs, pollutants, chemicals, contaminants, or the like. Regardless of the format for the assays, the analyte concentration is inferred from the dose-response curve. This can be done by finding the ordinate on the dose-response curve corresponding to the signal for the unknown concentration of analyte in the sample. The later quantity is given by the value of the abscissa. The dose-response curve is typically non-linear and it can be prepared by assaying standard samples containing known concentrations of the analyte. The number of standard samples and their concentrations are selected in order to determine the analyte concentrations with sufficient accuracy over the expected assay range.

A variation in the assay conditions, however, can modify the actual relationship between the measured signal and analyte concentration from that predicted by the initial dose-response curve. It is therefore often necessary for an analyzer to accurately control and maintain variables that affect the dose-response curve. One of the most common variables that produces significant variations in an assay signal is temperature. Changes in temperature lead to assay variations due to the strong thermal dependence of reaction rates and assay kinetics. For example, it is well known that the signal of a homogeneous enzyme assay, in which an enzyme is acting on a substrate to produce a measurable signal, has a thermal dependence of approximately 4% per degree Celsius.

In the past, automated analyzer systems have included complex thermal stabilization systems to ensure a constant and stable temperature during the analytic phase of an assay. For example U.S. Pat. No. 4,483,823A (Umetsu et al., filed 1982) describes an automated analyzer in which a water bath with precise temperature control is employed to regulate the temperature of a sample vessel. In another example of the prior art, U.S. Pat. No. 4,933,146 A (Meyer and Greene, filed 1986) discloses a thermal subsystem for the accurate thermal regulation of a set of cuvettes in an automated analyzer. An alternative method to avoid degradation in assay performance due to thermal sensitivity is to measure a full set of calibrators and obtain a new dose-response curve each time samples are analyzed. In such a scheme, it is only important to keep the temperature stable during the assay. Unfortunately, this method is not practical since most assays require many separate calibrators for proper calibration. Running several calibrators each time samples are assayed leads to significantly impaired throughput, increased costs and added complexity, especially when many analytes are analyzed in parallel.

An attempt to solve the problems associated with assaying multiple calibrators involves the use of internal multiplexed calibrators. Instead of assaying physically separate calibrators, in which standards containing known concentrations of single or multiple analytes are assayed in the same manner as samples, assay reagents are designed to give, in addition to a principal signal indicative of the analyte concentration, a calibration signal to correct for variations in the assay parameters.

U.S. Pat. No. 5,648,274 (issued to Chandler et al.) describes the use of a single internal calibrator in a comparative dual assay and U.S. Pat. No. 5,387,503 (issued to Selmer et al.) describes the use of an internal calibration by the addition of foreign analytes to samples and detection of both the target and foreign analytes at separate areas on a solid support. In a variation of these methods, the sequential addition to the assay reagents of a sample followed by the internal calibrator is described in U.S. Pat. No. 6,514,770 (issued to Sorin). The disadvantage of using an internal calibrator is that insufficient calibration measurements are obtained to properly re-calibrate the initial dose-response curve. Additional disadvantages include the requirement for dedicated reagents, which are not always commercially available, and an analyzer capable of detecting two signals. For these reasons, internal calibrators are not readily integrated into a commercial assay platform.

Recently, a general method of correcting for changes in an assay signal due to variations such a temperature was disclosed in copending U.S. patent application Ser. No. 11/072,651, filed Mar. 7, 2005 entitled "Correction for Temperature Dependence of Assays". This method involves assaying one or more additional calibrators each time samples are analyzed. In a preferred embodiment of this invention, no additional calibrator is added to the reagents and the inherent signal from the reagents themselves is used for assay calibration. Although this method produces satisfactory results for many different assay formats, its accuracy is limited when used with assays that exhibit thermal sensitivity due to complex mechanisms such as binding kinetics.

What is therefore required is a reliable method of accurately compensating for thermal variations in an assay signal that does not significantly impair assay throughput and can be applied to a wide range of assay formats.

SUMMARY OF THE INVENTION

The present invention provides assays and methods of compensating for changes in the dose-response curve of an assay where such changes are due to variations in a perturbing variable such as, but not limited to temperature.

Broadly, this is achieved by using two major steps, the first step of which involves measurements of the dose-response curve, and thus the individual assay parameters, at many different values of the perturbing variable, spanning the expected range of the perturbing variable. In the second step, unknown samples are assayed simultaneously with a known standard at a chosen analyte concentration. During this second step, the value of the perturbing variable is unknown and the dose-response curve is therefore also unknown. The different dose-response curves from the first step are used to determine a mathematical relationship between the assay parameters and the assay signal of the known standard. With this relationship, in which the value of the perturbing variable is implicit rather than explicit, assay parameters that are valid for the unknown value of the perturbing variable can be obtained by substituting the value of the assay signal from the known standard (measured when assaying the unknown samples) into the mathematical relationship and solving for the assay parameters. The method enables an accurate determination of the analyte concentration even when the perturbing variable is changing or fluctuating from one sample measurement to another. Once the first step is completed, the second step can be performed repeatedly to measure unknown samples with accuracy.

In one aspect of the invention there is provided a method of determining a dose-response curve of one or more assays, where the one or more assays is sensitive to the effects of a perturbing variable. The method first includes characterizing the dependence of the dose-response curve of one or more assays on the perturbing variable by the steps of:

i) measuring assay signals from a suitable set of known standards for the one or more assays at different values of the perturbing variable, and also measuring one or more other signals dependent on the perturbing variable, and whereby the one or more other signals dependent on the perturbing variable are measured for each of the different values of the perturbing variable;

ii) fitting the measured assay signals to a suitable functional form to produce a dose-response curve for each of the one or more assays at each of the different values of the perturbing variable and determining assay parameters from the fitting; and iii) establishing a mathematical relationship between each assay parameter of the one or more assays and each of the one or more other signals dependent on the perturbing variable.

Once the mathematical relationship has been established between each assay parameter of the one or more assays and each of the one or more other signals dependent on the perturbing variable, the assays are then performed on unknown samples. When performing one or more assays of unknown samples, a dose-response curve is determined that compensates for the effects of changes in the value of the perturbing variable by the steps of:

iv) re-measuring the one or more other signals dependent on the perturbing variable;

v) obtaining a value of each assay parameter of the one or more assays by substituting one of the one or more re-measured other signals dependent on the perturbing variable into the mathematical relationship between the assay parameter and the one of the one or more other signals dependent on the perturbing variable, and repeating the substitution for each of the one or more other signals dependent on the perturbing variable to obtain one or more values of the assay parameter; and vi) producing a compensated dose-response curve for each of the one or more assays of the unknown samples by averaging the one or more values of each assay parameter of the one or more assays.

In another aspect of the present invention there is provided a method of compensating a previously measured dose-response curve of one or more assays for the effects of a perturbing variable to which the one or more assays are sensitive, comprising the steps of first characterizing a dependence of a dose-response curve of one or more assays on the perturbing variable by the steps of:

i) measuring assay signals from a suitable set of known standards for the one or more assays at different values of the perturbing variable, and also measuring one or more other signals dependent on the perturbing variable, and whereby the one or more other signals dependent on the perturbing variable are measured for each of the different values of the perturbing variable;

ii) fitting the measured assay signals to a suitable functional form to produce a dose-response curve for each of the one or more assays at each of the different values of the perturbing variable and determining assay parameters from the fitting; and iii) establishing a mathematical relationship between each assay parameter of said one or more assays and each of said one or more other signals dependent on said perturbing variable.

Prior to performing assays on unknown samples, the dose-response curves of the one or more assays are measured. This process can be repeated periodically during routine use of the assays in order to correct for long-term assay variations. Periodic measurements of the dose-response curves of the one or more assays are obtained by measuring assay signals from a suitable set of known standards for the one or more assays and fitting the measured assay signals to a suitable functional form to produce a dose-response curve for each of the one or more assays. When measuring the dose-response curves, the one or more other signals dependent on the perturbing variable are also measured.

When performing one or more assays of unknown samples, the previously measured dose-response curves of the one or more assays are compensated for the effect of a change in the perturbing variable by the steps of:

iv) re-measuring the one or more other signals dependent on the perturbing variable;

v) obtaining a compensated value of each assay parameter of said one or more assays by adding to each assay parameter obtained from said previously measured dose-response curve for said one or more assays a value equal to the difference between an assay parameter calculated by said mathematical relationship by substituting one of said one or more signals dependent on said perturbing variable re-measured with said assays for said unknown samples, and an assay parameter calculated by said mathematical relationship by substituting one of said one or more signals dependent on said perturbing variable measured with said previously measured dose-response curve, and repeating steps iv) and v) for each of said one or more other signals dependent on said perturbing variable to obtain one or more values of said each assay parameter; and vi) producing a compensated dose-response curve for each of the one or more assays of the unknown samples by averaging the one or more values of each assay parameter for each of the one or more assays.

A further understanding of the functional and advantageous aspects of the invention can be realized by reference to the following detailed description and drawings.

BRIEF DESCRIPTION OF THE DRAWINGS

The invention will be more fully understood from the following detailed description thereof taken in connection with the accompanying drawings, which form a part of this application, and in which:

FIGS. 2 to 5 show, respectively, plots of assay parameters $a_1$, $a_2$, $a_3$ and $a_4$ as a function of signal at a concentration of 2500 ng/ml, for a sigmoidal dose-response curve written as:

$$S = a_2 + \frac{a_1 - a_2}{1 + (C/a_3)^{a_4}}, \text{ and}$$

Figure 1:
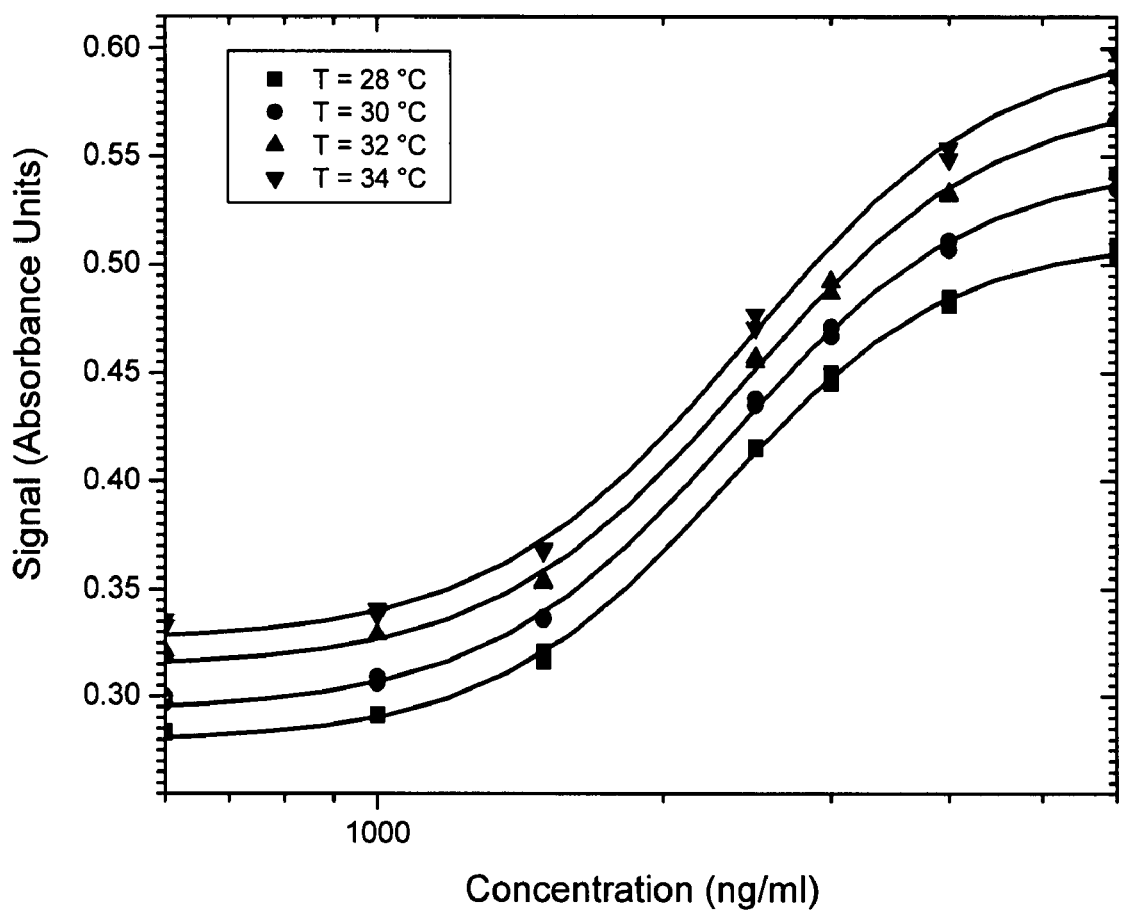
FIG. 1 shows dose-response curves (absorbance vs concentration) for a set of calibrators made at different temperatures.
Figure 2:
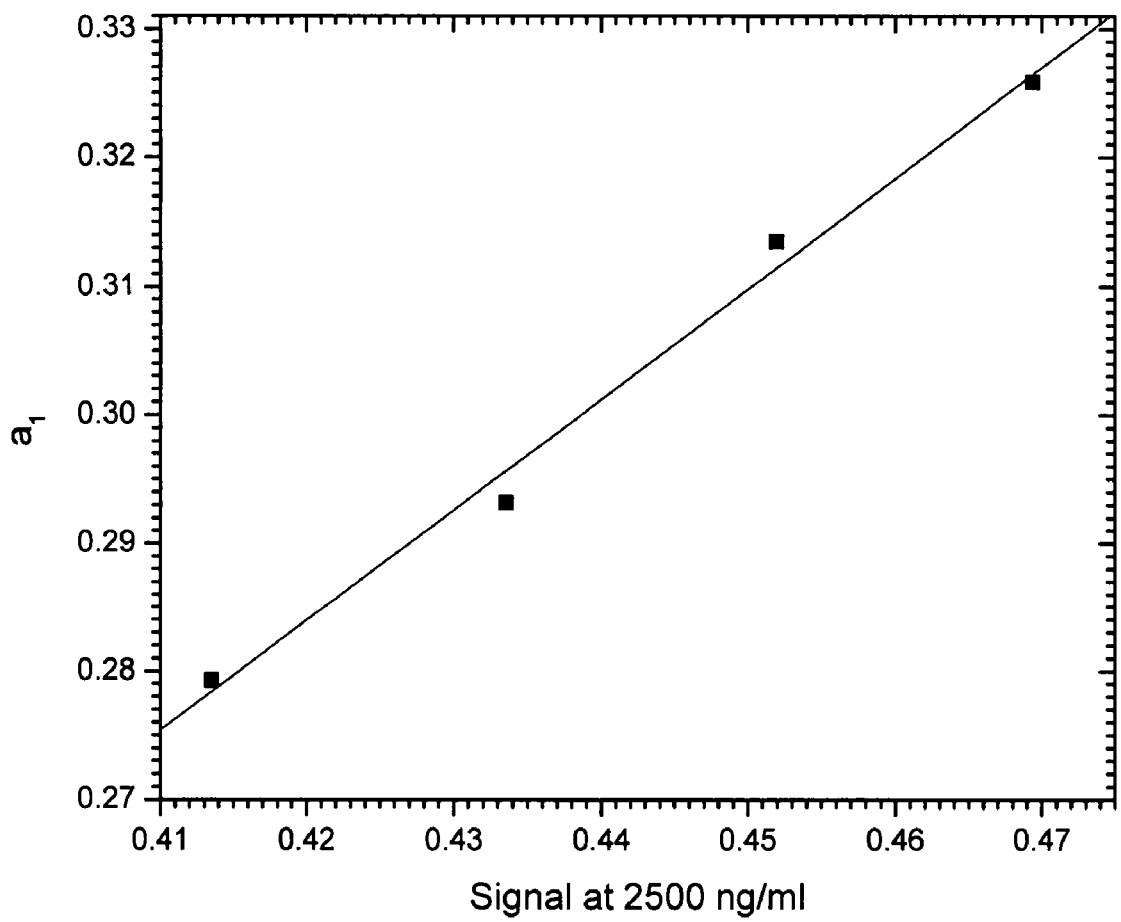
Figure 3:
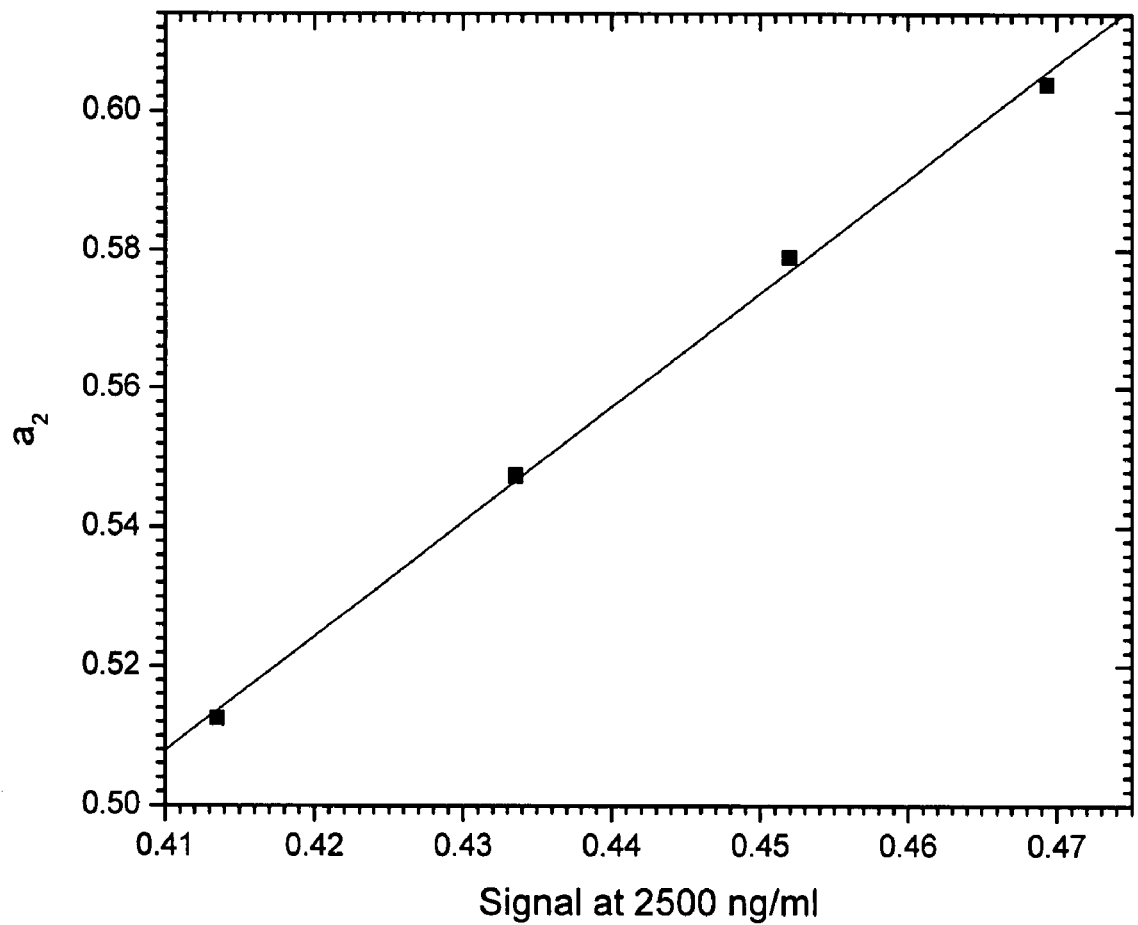
Figure 4:
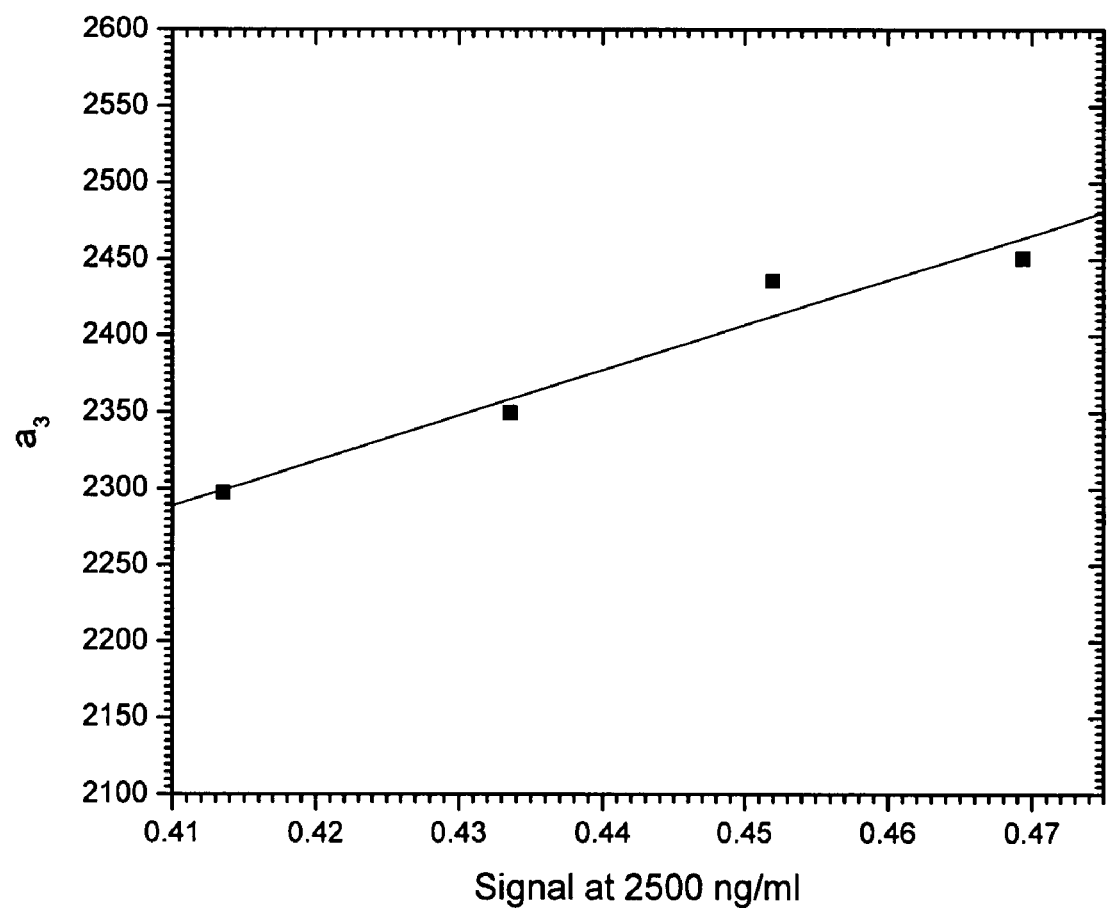
Figure 5:
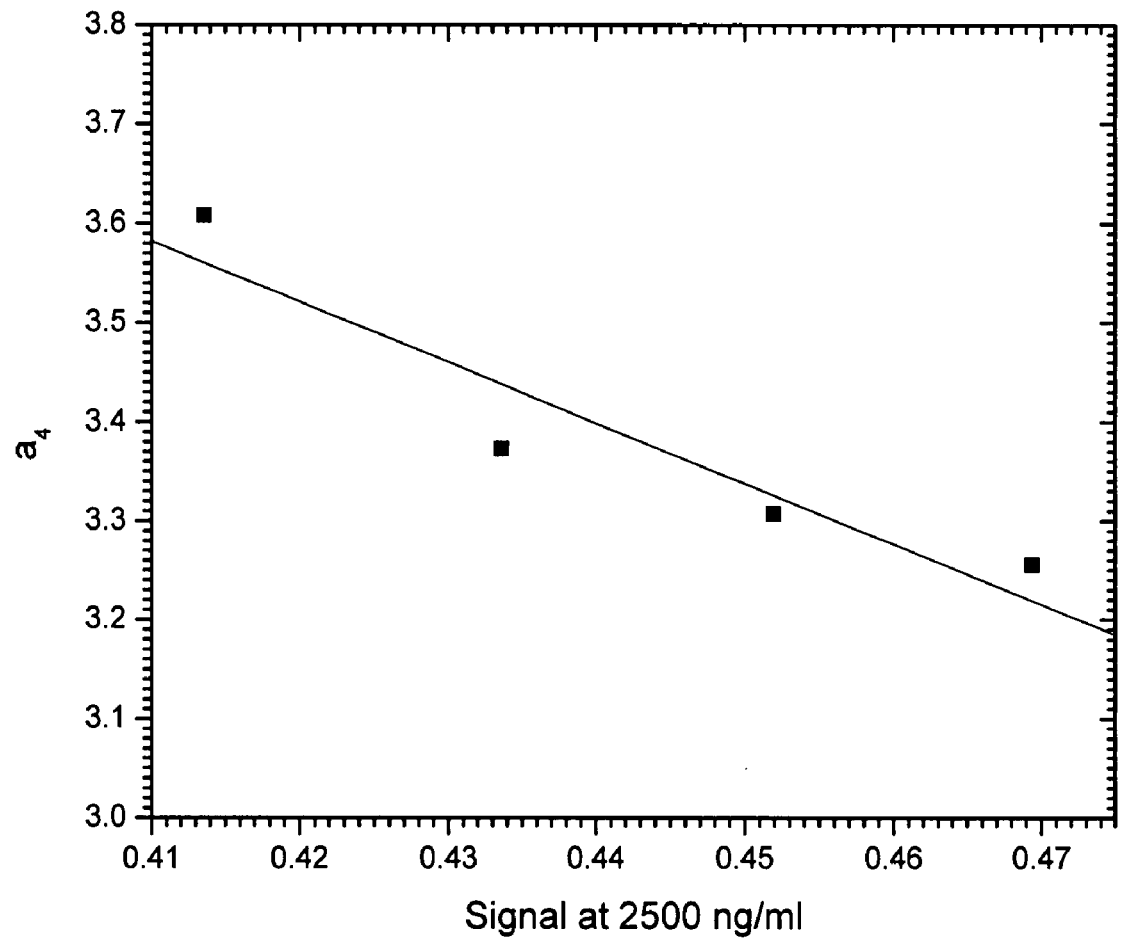
Figure 6:
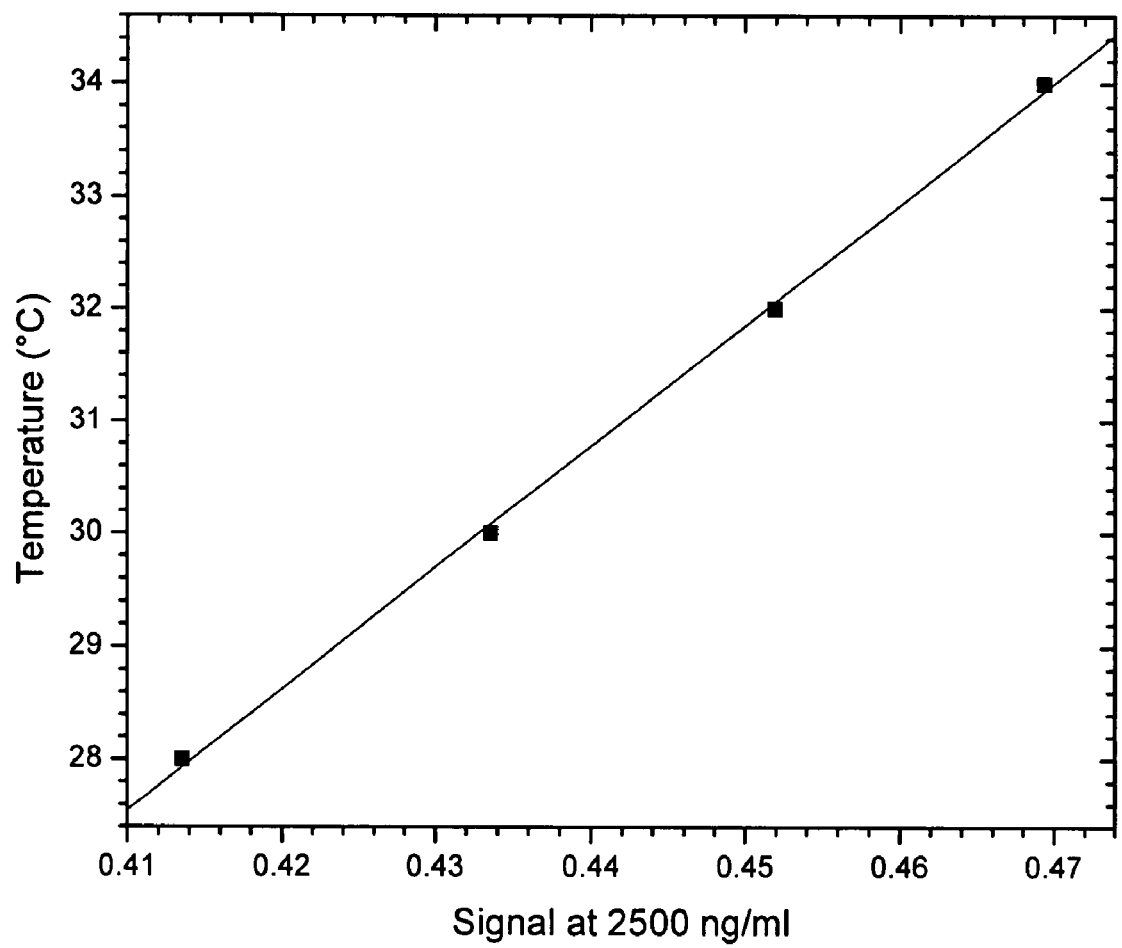

FIG. 6 shows a plot of temperature which is also plotted against $S_{cal}$ in corresponding to the FIGS. 2 to 5.

Figure 7:
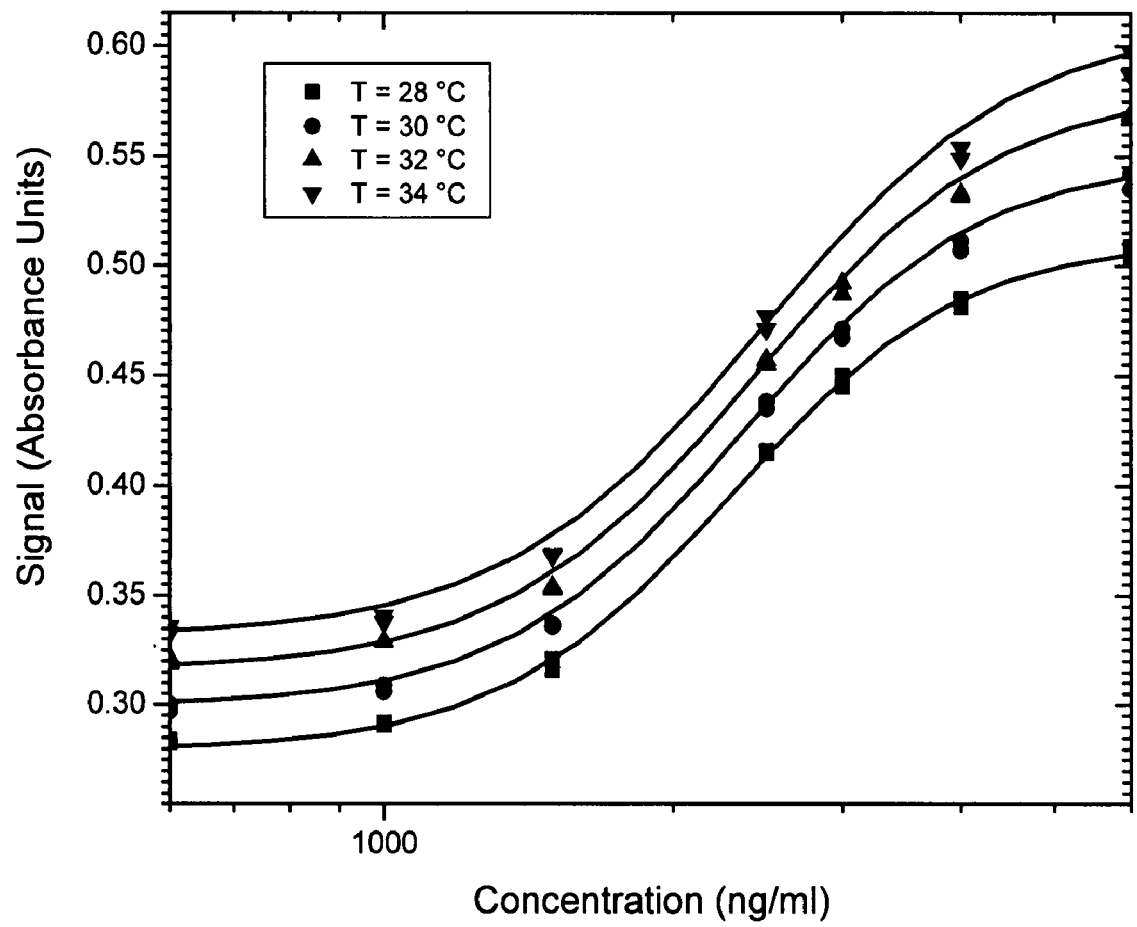

FIG. 7 shows the calibration dose-response curve (at 28° C.) along with both the thermally-compensated curves and measured data points for the three additional temperatures (at 30, 32 and 34° C.).

DETAILED DESCRIPTION OF THE INVENTION

Generally speaking, the systems described herein are directed to methods of compensation of dose-response curve of an assay for sensitivity to perturbing variables. As required, embodiments of the present invention are disclosed herein. However, the disclosed embodiments are merely exemplary, and it should be understood that the invention may be embodied in many various and alternative forms. The Figures are not to scale and some features may be exaggerated or minimized to show details of particular elements while related elements may have been eliminated to prevent obscuring novel aspects. Therefore, specific structural and functional details disclosed herein are not to be interpreted as limiting but merely as a basis for the claims and as a representative basis for teaching one skilled in the art to variously employ the present invention. For purposes of teaching and not limitation, the illustrated embodiments are directed to methods of compensation of dose-response curve of an assay for sensitivity to perturbing variables.

As used herein, the term "about", when used in conjunction with ranges of dimensions including volume, weight, temperatures or other physical properties or characteristics is meant to cover slight variations that may exist in the upper and lower limits of the ranges so as to not exclude embodiments where on average most of the dimensions are satisfied but where statistically dimensions may exist outside this region.

As used herein, the phrase "performing an assay" or "assaying" means following a pre-determined set of steps in order to obtain and measure a signal related to an unknown concentration of an analyte present in a sample, and where a known relationship between the signal and the analyte concentration is employed to infer the analyte concentration.

As used herein, the phrase "dose-response curve" means a mathematical function that describes the relationship between an assay signal and an analyte concentration.

As used herein, the phrase "an assay parameter" means a coefficient in the dose-response curve of an assay.

As used herein, the phrase "perturbing variable" means a variable to which an assay signal is sensitive, whereby variations in the perturbing variable produce variations in the assay signal.

As used herein, the phase "assay signal" means a measurable quantity resulting from an assay reaction, such as optical density, luminescence power, fluorescence power, or changes in any of these quantities during a reaction.

As used herein, the phase "a signal dependent on a perturbing variable" means any measurable quantity that depends on the value of the perturbing variable, such as optical density, luminescence, fluorescence, or changes in any of these quantities during a reaction. The phase "a signal dependent on a perturbing variable" may also be a direct measurement of the perturbing variable, such as a measurement of temperature if the perturbing variable is temperature.

As used herein, the phrase "a signal-generating means that produces a signal related to the value of the perturbing variable" means a material, transducer or other device that produces a signal that is directly related to the value of the perturbing variable.

As used herein, the phrase "an outlier test" means a statistical test designed to detect the presence of outliers in a dataset.

As used herein, the phrase "compensation function" means a mathematical relationship between an assay parameter and a signal dependent on a perturbing variable.

As used herein, the phrase "compensation coefficient" means the slope of a linear relationship between an assay parameter and an assay signal dependent on a perturbing variable.

Biological assays are characterized by a dose-response curve that describes the relationship between the measured assay signal and the corresponding analyte concentration. The dose-response curve is usually fitted to a specific functional form, the most common functional forms being the sigmoidal and linear functions. In general, a dose-response curve can be written as a signal S that is given by a function F, where the function F is dependent on the analyte concentration C and a set of mathematical parameters $a_n$:

$$S = F(C; a_1, a_2, \ldots, a_n, \ldots, a_N) \quad (1)$$

For example, a sigmoidal dose-response curve is written as:

$$S = a_2 + \frac{a_1 - a_2}{1 + (C/a_3)^{a_4}}, \quad (2)$$

where the assay parameters $a_1$, $a_2$, $a_3$ and $a_4$ specify a particular curve among the infinite family of sigmoidal curves.

Equations (1) and (2) are static dose-response curves that are only valid when the assay conditions are stable and constant. In reality, the true dose-response relationship fluctuates in time due to changes in perturbing variables to which the assay signal is sensitive. For example, it is well known that most assays are strongly dependent on changes in temperature. If changes in a perturbing variable produce variations in the dose-response curve, then equations (1) and (2) must be modified as follows:

$$S(C, x) = F[C; a_1(x), a_2(x), \ldots, a_n(x), \ldots, a_N(x)], \quad (3)$$

$$S(C, x) = a_2(x) + \frac{a_1(x) - a_2(x)}{1 + [C/a_3(x)]^{a_4(x)}}, \quad (4)$$

where x denotes the value of the perturbing variable to which the assay is sensitive. If the perturbing variable is itself changing during the assay (i.e. equilibrium has not been reached), then x can be interpreted, in a first approximation, as the average value of the variable during the assay analytic phase.

Although there may be special cases where some of the assay parameters are insensitive to changes in a perturbing variable (i.e. $da_n/dx=0$), it is common for all parameters to exhibit significant and unique dependencies on changes in a perturbing variable. For example, the assay parameters of an enzymatic assay usually each depend on temperature in a unique way. In general, the dependence of any given assay parameter will be a nonlinear function of x that is best determined experimentally.

The inventors have discovered that a novel and effective method can be employed to compensate for the dependence of the dose-response curve of an assay on changes in a known perturbing variable. This is achieved by a two-step method, the first step of which involves measurements of the dose-response curve (and thus the individual assay parameters) at many different values of the perturbing variable (with the values spanning an expected range of the perturbing variable). In the second step, unknown samples are assayed simultaneously with a known standard at a chosen analyte concentration. During this measurement, the value of the perturbing variable is unknown and the dose-response curve is therefore also unknown.

Despite the uncertainty in values of the perturbing variable and the dose-response curve when the unknown samples are assayed, the measurement of the known standard enables the determination of the new dose-response curve. This is achieved as follows: the different dose-response curves from the first step are used to determine a mathematical relationship between the assay parameters and the assay signal of the known standard. With this relationship, in which the value of the perturbing variable is implicit rather than explicit, assay parameters that are valid for the unknown value of the perturbing variable can be obtained by substituting the value of the assay signal from the known standard (measured when assaying the unknown samples) into the mathematical relationship and solving for the assay parameters. The method therefore enables an accurate determination of the analyte concentration even when the perturbing variable is changing or fluctuating from one sample measurement to another. Furthermore, once the first step is completed, the second step can be performed repeatedly to measure unknown samples with accuracy.

The detailed steps of the method are described as follows. In a preliminary measurement phase, the assay signals from a set of known standards (several samples with known analyte concentrations) are measured at a number of different values of the perturbing variable over the range of interest of the perturbing variable. Dose-response curves and assay parameters ($a_n$) are obtained for each different value of the perturbing variable by fitting the measured assay signals from the known standards to a chosen functional form. A sufficient number of standards are included to obtain a good fit over the desired range of analyte concentrations, with the goodness of fit determined by statistically meaningful measures such as the $\chi^2$ or $R^2$ parameters.

A known standard, with a concentration $C_{cal}$, is chosen to be assayed when later performing assays on unknown samples. The signal values $S_{cal}$ corresponding to the concentration $C_{cal}$ at each of the different values of the perturbing variable are then obtained from the measured dose-response curves. This is done by substituting $C_{cal}$ into the dose-response equations and solving for S (for the sigmoidal function this would be equation 2 above). The concentration $C_{cal}$ is preferably chosen to give a sufficiently high signal-to-noise ratio in the assay signal (note that the concentration may be chosen to be below the lower limit of quantitation if this criteria is satisfied). The dependence $a_n(S_{cal})$ of each assay parameter on the calibrator signal can then be determined by fitting the observed values of the assay parameters and the calibrator signal to an appropriate mathematical function (e.g. a linear or higher order polynomial function). This function must be single-valued of the expected range of values of the perturbing variable.

This preliminary measurement phase characterizes the dependence of the assay on the perturbing variable via the mathematical relationships $a_n(S_{cal})$. These relationship, to be henceforth referred to as the compensation functions, can then be used in subsequent assays for samples with unknown analyte concentrations in order to provide an accurate determination of the analyte concentration despite variations in the value of the perturbing variable. When measuring samples with unknown analyte concentration, at least one known standard having the concentration $C_{cal}$ is also measured. It is important to note that in this context, the term "when" implies that the measurement of the known standard are to be performed at a time that is approximately equal to the time of measurement of the unknown samples, so that the value of the perturbing variable is approximately the same for all measurements. The known standard can include multiple analytes, in which case it could be used as a standard for multiple assays that are each compensated via the present method. The value of the measured signal from the standard is denoted as $S_{cal}'$.

The value of the perturbing variable at which the samples and the standard are measured is denoted as x' and is generally unknown, especially if careful provisions have not been made to keep the perturbing variable constant. The compensation functions are used to produce a corrected dose-response curve that is valid and accurate for the present value of the variable x' by substituting $S_{cal}$ into the compensation functions:

$$a_n(x')=a_n(S_{cal}'). \qquad (5)$$

Finally, the compensated assay parameters $a_n(x')$ are used in the dose-response curve to correctly infer the analyte concentrations of the samples. Since the assay parameters have been accurately corrected for variations in the perturbing variable, an assay with accuracy and precision can be performed even when changes in the perturbing variable occur.

In principle, once the dependence of the dose-response curve on the variable has been measured and quantified by the compensation functions, it is not per se necessary to re-measure the dose-response curve. However, in practice, it is common to periodically re-measure a dose-response curve for the purpose of re-calibrating the assay for potential variations in other variables (for example systematic errors in liquid handling or long term degradation of the reagents). In such cases, when subsequently measuring samples with unknown analyte concentrations, it may be advantageous to depart from the aforementioned method and instead compensate a previously measured calibration dose-response curve. This method, in contrast to the method described previously, only compensates for the change in the value of the perturbing variable relative to its value during the measurement of the calibration dose-response curve.

This can be achieved using equation (5) to use the change in the value of the calibrator signal $S_{cal}$ to calculated the change in a given assay parameter $a_n$, according to the following equation:

$$a_n(x')=a_n^0+[a_n(S_{cal}(x'))-a_n(S_{cal}(x_0))], \qquad (6)$$

where $x_0$ and $S_{cal}(x_0)$ are the value of the perturbing variable and the assay signal from the known standard at the point in time at which the calibration dose-response curve was previously measured, respectively. This method differs from the aforementioned method of equation 5 by only using the compensation functions to calculate the change in the assay parameters relative to a previously measured dose-response curve.

This method has particular utility when the compensation functions are well fit by a linear relationship. For example, the inventors have found that when the perturbing variable is temperature, the compensation functions are linear to a very good approximation over a wide temperature range for several different assays. In such cases, the compensation functions can be rewritten in the form:

$$a_n(x) = a_n^0 + a_n^1 S_{cal},  \quad (7)$$

where $a_n^1$, is the slope and will be henceforth referred to as the compensation coefficient for a particular $a_n$.

Equation 6 can be rewritten to compensate a previously measured dose-response curve for subsequent variations in the variable according to the following equation:

$$a_n(x') = a_n(x_0) + a_n^1 [S_{cal}(x') - S_{cal}(x_0)],  \quad (8)$$

again where $x_0$ and $S_{cal}(x_0)$ are the value of the perturbing variable and the assay signal from the known standard at the point in time at which the calibration dose-response curve was previously measured, respectively. $S_{cal}(x_0)$ is obtained by solving the calibration dose-response curve for S at the concentration $C_{cal}$.

It should be noted that it may also be possible to transform a nonlinear dependence on the assay signal from the known standard into a linear dependence in certain situations. In such cases, equations 7 and 8 can be replaced by:

$$T\{a_n(x)\} = a_n^0 + a_n^1 S_{cal}  \quad (9)$$

$$T\{a_n(x')\} = T\{a_n(x_0)\} + a_n^1 [S_{cal}(x') - S_{cal}(x_0)],  \quad (10)$$

where T{ } represents the transformation.

Equation 5 may appear to be advantageous over equation 6 due to the fact that in equation 5, the compensated assay parameters are directly calculated from compensation functions. However, in practice, the second method yielding equation 6 may offer superior performance when the dose-response curve is sensitive to multiple variables. Since the second method permits multiple measurements of the dose-response curve and only corrects for changes in the variable relative to the most recently measured dose-response curve, long-term variations caused by other variables may also be corrected. Therefore, in certain cases, the dose-response curve itself may shift without having any consequence on the validity of the compensation. This may offer particular utility if long-term aging of the assay reagents causes global shifting of the curves, in which case the shift will be compensated via the newly measured dose-response curve.

It may be desirable to improve the above method by adding a control mechanism to validate the accuracy of the compensated dose-response curve. This can be done, for example, by assaying, in addition to the unknown samples and the known standard, additional known standards to serve as controls. The assay signals from the controls are substituted into the compensated dose-response curve and the resulting equation is solved to obtain the control concentrations. If the measured concentrations, when compared to the known concentration of the standard, pass a predetermined criterion, the dose-response curve is deemed to be accurate.

It is also possible to improve the precision of the assay by assaying one or more replicates of a known standard when assaying unknown samples. The replicate signals can be first analyzed to determine whether or not an outlier has occurred (using, for example, one of many outlier tests known to those skilled in the art). If an outlier is found, the assay run is rejected. If no outlier is found, then prior to performing the calculation in equation 5 or 6 (depending on which method is chosen), the replicate signals $S_{cal}$ are first averaged to a more precise result. In another embodiment, known standards with different concentrations (i.e. different values of $C_{cal}$ and $S_{cal}$) can be assayed together. Instead of averaging the different signal values, each known standard is used to generate a set of compensated assay parameters via the aforementioned methods. Outlier tests are then performed on each of the assay parameters, and the assay run is rejected if any outliers are found. The multiple values of the compensated assay parameters are then averaged to a more precise result. In a third embodiment, the two methods can be combined if desired.

In the above description, the assay signal from a known standard has been used as a signal dependent on the perturbing variable. In some cases, the assays signal can advantageously provide a direct measurement of an assay parameter. For example, in the case of an assay with a dose-response curve that is described by a sigmoid (i.e. equation 2), an assay reaction with the absence of analyte provides a signal with a value equal to $a_1$.

This can have particular relevance to sigmoid assays that are susceptible to more than one perturbing variable, where one global perturbing variable potentially affects all assay coefficients, while the other perturbing variables only affect $a_1$ and $a_2$, provided that all perturbing variables affect $a_1$ and $a_2$ in a similar fashion, i.e. provided that the dependence of $a_2$ on $a_1$, i.e. $a_2(a_1)$, substantially holds irrespective of which perturbing variable causes a change in these two assay parameters. In this case, the first signal dependent on a perturbing variable can be a direct measurement of $a_1$, as described in the above paragraph. This signal can clearly be used to provide a compensated value of $a_1$ that corrects for all perturbing variables. If $a_2$ exhibits a dependence on $a_1$ that holds regardless of which perturbing variable causes a change in $a_1$, then $a_2$ can be thermally compensated via the relationship $a_2(a_1)$, which is measured by varying the global perturbing variable only. If $a_3$ and $a_4$ are only substantially dependent on the global perturbing variable, they can be thermally be compensated by a second signal dependent on the global perturbing variable, where this second signal is itself not dependent on the other perturbing variables.

An example of this scheme involves the compensation of a sigmoid assay for changes reagent quantity and changes in temperature. In this case, it is assumed that changes in the quantity of reagents primarily affect $a_1$ and $a_2$ and, for small changes in quantity, have a minimal effect on $a_3$ and $a_4$, while changes in temperature affect all assay parameters. Moreover, the relationship $a_2(a_1)$ is substantially similar for both changes in temperature and changes in reagent quantity. This behaviour has been observed hold for a class of homogeneous enzyme immunoassays. A direct measurement of $a_1$ as the first signal dependent on temperature can therefore be employed to correct for perturbations in reagent quantity and temperature. A direct measurement of temperature can be used as a second signal that is used to compensate only $a_3$ and $a_4$, since a temperature measurement does not depend on reagent quantity. Therefore, corrections of additional perturbations due to changes in reagent quantity can be incorporated into the compensation scheme.

A practical example of the above method is now considered for the case of an assay in which the enzyme-multiplied immunoassay technique (EMIT) is used for the detection of the concentration of the metabolite of methadone in urine. The assay is homogeneous and is based on the competition of an enzyme-labeled drug conjugate with drug in the sample for a finite number of antibodies. The binding of the drug conjugate to the antibody decreases the activity of the enzyme, which produces a measurable signal when the enzyme is made to act on a chromogenic substrate. In this case, since the assay is most sensitive to thermal perturbations, the invention is employed to compensate for variations in temperature.

In the preliminary measurement phase, multiple measurements of a set of calibrators are made at different temperatures. The resulting dose-response curves are shown in FIG.

1. For this assay, the dose-response curves are well fitted by a sigmoidal functional form (see equation 2). The concentration of the known standard to be assayed with an unknown sample is chosen to be 2500 ng/ml. Plotting the various $a_n$ parameters as a function of $S_{cal}$, the signal predicted from the dose-response curves at a concentration of 2500 ng/ml, one obtains FIGS. 2-5. Since the temperatures corresponding to the measurements during the preliminary phase are known, temperature is also plotted against $S_{cal}$ in FIG. 6. One clearly observes that all of the data plotted in FIGS. 2-6 follows a linear relationship. Therefore, the second method of compensation is chosen in which the dependencies of the assay parameters on the signal from the known standard are fitted to a linear relationship according to equation 7. After employing linear regression to fit the data to a straight line, the compensation coefficients $a_n^1$ are obtained from the fitted slope. The dependence of the measured temperature on the signal from the known standard is fitted to a linear relationship as it is best described in this case by a straight line. This latter fitting procedure provides a supplementary relationship $T(S_{cal})$ that can be used to determine the temperature when performing assays on unknown samples.

With all compensation coefficients determined, the dose-response curve measured during a calibration assay (with multiple standards having known concentrations) can be accurately thermally compensated via the measurement of the known standard whenever unknown samples are measured. In order to demonstrate the accurate thermal compensation of the dose-response curve, the data used to generate the compensation coefficients in the above example is also used to show self-consistent results. In this example, the data taken at 28° C. is used to generate the calibration dose-response curve. The data at all other temperatures is taken to be real sample data, with the exception of the data at 2500 ng/ml, which is taken to be the signal from the known standard. For each of the three other temperatures, the dose-response curve from initial calibration (at 28° C. data) is thermally compensated using equation 8.

The results of thermal compensation are shown in FIG. 7, in which the calibration dose-response curve (at 28° C.) is shown along with both the thermally-compensated curves and measured data points for the three additional temperatures. It is emphasized here that the three thermally-compensated dose-response curves (at 30, 32 and 34° C.) are not obtained from a nonlinear fitting procedure in which multiple standards are fitted, but are rather obtained from the initial calibration dose-response curve using only the signal from the known standard via equation 8. As shown in FIG. 7, the thermally-compensated curves accurately fit the measured data, thus confirming the utility of equation 8 in a self-consistent manner.

Although the above embodiments have required the use of a signal from a known standard to compensate the dose-response curve, one may also perform the invention by measuring any signal that is related to the perturbing variable, even if the signal is not obtained via the assay being compensated. This is achieved by modifying the preliminary measurement phase so that in addition to measuring assay signals from a set of known standards at each value of the perturbing variable, a signal related to the perturbing variable is also measured. This signal may be a direct measurement of the variable (e.g. the measurement of temperature with a thermometer) or an indirect measurement of a signal related to the perturbing variable (e.g. the indirect measurement of temperature via an enzymatic reaction producing a colourimetric response). This enables a determination of the dependence $a_n(S)$ of the assay parameters on the signal related to the perturbing variable, which is obtained by fitting the observed values to a chosen functional form. When subsequently assaying unknown samples, or when periodically measuring the dose-response curve, this signal related to the perturbing variable is again measured. In this generalization, equations 5-8 are then modified by replacing $S_{cal}$, the signal from a known calibrator, with S, a signal related to the perturbing variable. It is important to note that in order for this method to be effective, the relationship between the signal S and the perturbing variable x must be single-valued over the expected range of the perturbing variable.

The above embodiments, including the preceding generalization to any signal related to the perturbing variable, can be further generalized by noting that the signal related to the perturbing variable can be employed to compensate for more than one assay at a time. This is achieved by modifying the preliminary measurement phase to include a characterization of the dependence of the dose-response curves of several assays (instead of a single assay) on the perturbing variable via the measurement of the assay signals from a set of standards for each assay at different values of the perturbing variable, and also measuring a signal related to the perturbing variable. By fitting the measured signals for the known standards to the appropriate mathematical functions, dose-response curves and assay parameters are obtained for each assay. The dependence of the assay parameters for each assay on the signal related to the perturbing variable is then fitted to a known mathematical function to obtain the compensation functions $a_n(S)$ if the method of equation 5 is used. On the other hand, if the method of equation 8 is used, the dependence of the assay parameters for each assay on the signal related to the perturbing variable is fitted to a linear function and the slope is obtained according to equation 8 for each assay parameter of each assay.

In certain cases, the mathematical relationship between an assay parameter and the signal dependent on the perturbing variable may be double-valued in the assay parameter, i.e. there may be two possible assay parameter values for a single value of the signal dependent on the perturbing variable. In this case, a second signal dependent on the perturbing variable may be used to compensate the particular assay parameter, provided that the second signal dependent on the perturbing variable is related to the particular assay parameter in a one-to-one fashion.

It is important to note that during the preliminary measurement phase, if multiple assays are performed together, at approximately the same time, then the value of the perturbing variable must be significantly uniform among all assays. When measuring unknown samples for any of the assays, the signal related to the perturbing variable is also measured. Furthermore, if the method of equations 6 or 8 is used, the signal related to the perturbing variable is also measured when periodically measuring the dose-response curve of any of the assays. This enables the dose-response curve of any assay to be updated according to either equation 5, 6 or 8, where the assay parameters $a_n$ are taken to be assay parameters of any of the assays considered.

In another embodiment of the invention, in which the signal related to the perturbing variable is an assay signal from a known standard, the signal from the known standard is used to further improve the accuracy of the compensated dose-response curve. Since the analyte concentration of the standard is known, the compensated dose-response curve can be forced to pass through the data point produced by the assay signal of the standard (i.e. the assay signal and analyte concentration).

This is achieved as follows. Initially, all assay parameters are compensated using either equation 5, 6 or 8, depending on the preferred method. One assay parameter is then selected to be further compensated via the assay signal of the known standard. The assay signal and concentration from the known standard are substituted into the compensated dose-response curve, and the resulting equation is solved for the selected assay parameter. This method can also be used when multiple assays are compensated via the measurement of a known standard belonging to one of the multiple assays. In that case, the dose-response curve of the assay to which the known standard belongs can be improved using this method.

The above embodiment can have particular utility for assays that make use of a cutoff concentration. A cutoff is a concentration that represents a decision point. Samples with concentrations above and below the cutoff are labelled as positive and negative, respectively. The consequence of a sample being positive or negative differs among applications, but is often therapeutic or legal in nature. For example, when performing screening assays for drugs of abuse, a sample that is found to be positive will lead the test administrator to conclude that the individual being tested may be using illegal drugs (in this application, samples found to be high are usually confirmed using a reference test method). It may therefore be desirable to improve the accuracy of the compensation method in the vicinity of the cutoff. If, in the preceding embodiment, the concentration of the known standard is chosen to be the cutoff concentration, then the compensated dose-response curve is forced to pass through the measured cutoff data point. This enables an accurate positive-negative determination and enhances the specificity and sensitivity of the assay.

The preceding embodiment, involving the substitution of the signal and concentration of a known standard into the dose-response curve to directly solve for a selected assay parameter, can be generalized by measuring multiple standards at different concentrations rather than a single standard and directly compensating more than one assay parameter. A set of averaged assay parameters are first obtained according to the aforementioned embodiment in which multiple standards are measured to obtain an assay with improved precision. One of the known standards and one compensated assay parameter are then selected. The assay signal and concentration from the known standard are substituted into the dose-response curve, and the resulting equation is solved for the assay parameter. This process is repeated for each known standard, and a new dose-response curve is obtained by incorporating the newly compensated assay parameters.

A quality control mechanism can be incorporated into the above embodiments to provide a determination of the validity of the compensated dose-response curve. In the preceding two embodiments, an improved value of a selected assay parameter is obtained by substituting a selected assay signal and concentration of a known standard into the compensated dose-response curve and solving for the selected assay parameter. This provides two values for the selected assay parameter; an original value obtained using either equations 5, 6 or 8 (depending on the preferred method), and a new value obtained via the method of substitution. The two values can be compared and pass/fail criteria can be established for the difference between the two values, which, in theory, should be exactly equal.

In a preferred embodiment, two or more known standards are used for both compensation and quality control. This is achieved via the following method. Initially, the dose-response curve is compensated using a single one of the known standards according to equations 5, 6 or 8 (depending on which method is preferred). The compensated assay parameters are recorded and the compensated dose-response curve is used to estimate the concentrations of the remaining known standard. The known concentrations of the remaining known standards are compared to their estimated values, and are thereby used as controls to verify the accuracy of the initial compensation. This process is then repeated for the second known standard, with the other known standards being used as controls to verify the accuracy of the compensation based on the second known standard. This process is repeated for each known standard. If each compensated dose-response curve based on each known standard is deemed to have passed the quality control pass/fail criteria, then the compensated assay parameters obtained for each of the known standards are averaged and the average parameters are used to construct the final compensated dose-response curve.

A useful example of the above method involves incorporating two known standards with concentrations above and below the assay cutoff concentration. The dose-response curve is first compensated using the signal from the low standard (with a concentration below the cutoff concentration). The high standard (with a concentration above the cutoff concentration) is used as a control to verify the accuracy of the compensated dose-response curve. The same procedure is then repeated, but with the compensation based on the signal from the high standard and the low standard being used as a control. Upon obtaining acceptable results from the two standards, the compensated dose-response curve is obtained by averaging the two sets of assay parameters obtained using the low and high standards for compensation. The known standards, when used as controls, therefore provide high and low controls that ensure that the compensation method is working properly and also that there are no other problems in the measurement that could lead to the reporting of an erroneous result. Furthermore, the use of known standards with concentrations near to that of the cutoff enhances the accuracy of the dose-response curve at the cutoff concentration.

As used herein, the terms "comprises", "comprising", "including" and "includes" are to be construed as being inclusive and open ended, and not exclusive. Specifically, when used in this specification including claims, the terms "comprises", "comprising", "including" and "includes" and variations thereof mean the specified features, steps or components are included. These terms are not to be interpreted to exclude the presence of other features, steps or components.

The foregoing description of the preferred embodiments of the invention has been presented to illustrate the principles of the invention and not to limit the invention to the particular embodiment illustrated. It is intended that the scope of the invention be defined by all of the embodiments encompassed within the following claims and their equivalents.

Therefore what is claimed is:

1. A method of compensating a previously measured dose-response curve of one or more assays for the effects of a perturbing variable to which said one or more assays are sensitive, comprising the steps of:
   A) characterizing a dependence of a dose-response curve of one or more assays on said perturbing variable by the steps of,
   i) measuring assay signals from a suitable set of known standards for said one or more assays at different values of said perturbing variable, and also measuring one or more other signals dependent on said perturbing variable, and whereby said one or more other signals dependent on said perturbing variable are measured for each of said different values of said perturbing variable;

ii) fitting said measured assay signals to a suitable functional form to produce a dose-response curve for each of said one or more assays at each of said different values of said perturbing variable and determining assay parameters from said fitting; and iii) establishing a mathematical relationship between each assay parameter of said one or more assays and each of said one or more other signals dependent on said perturbing variable;

B) periodically measuring said dose-response curves of said one or more assays by measuring assay signals from a suitable set of known standards for said one or more assays and fitting said measured assay signals to a suitable functional form to produce a dose-response curve for each of said one or more assays and when measuring said dose-response curves, also measuring said one or more other signals dependent on said perturbing variable;

C) when performing one or more assays of unknown samples, compensating for the effect of a change in said perturbing variable on a previously measured dose response curve for said one or more assays, where said one or more other signals dependent on said perturbing variable were measured with said previously measured dose-response curve for said one or more assays, by the steps of:

iv) re-measuring said one or more other signals dependent on said perturbing variable;

v) obtaining a compensated value of each assay parameter of said one or more assays by adding to each assay parameter obtained from said previously measured dose-response curve for said one or more assays a value equal to the difference between an assay parameter calculated by said mathematical relationship by substituting one of said one or more signals dependent on said perturbing variable re-measured with said assays for said unknown samples, and an assay parameter calculated by said mathematical relationship by substituting one of said one or more signals dependent on said perturbing variable measured with said previously measured dose-response curve;

and repeating steps iv) and v) for each of said one or more other signals dependent on said perturbing variable to obtain one or more values of said each assay parameter; and vi) producing a compensated dose-response curve for each of said one or more assays of said unknown samples by averaging said one or more values of each assay parameter for each of said one or more assays.

2. The method according to claim 1 wherein step C) is repeated one or more times between said periodic measurements of said one or more dose-response curves.

3. The method according to claim 1 wherein said one or more other signals dependent on said perturbing variable are first and second signals that each exhibit a unique dependence on said perturbing variable, and where said second signal dependent on said perturbing variable is used in place of said first signal dependent on said perturbing variable for any of said one or more assays if said mathematical relationship between an assay parameter of said one or more assays and said first signal dependent on said perturbing variable is double-valued in said assay parameter.

4. The method according to claim 1 wherein said one or more other signals dependent on said perturbing variable are direct measurements of an assay parameter of one of said one or more assays.

5. The method according to claim 1 wherein said one or more signals dependent on said perturbing variable are direct measurements of one assay parameter from each of said one or more assays.

6. The method according to claim 1 wherein said one or more other signals dependent on said perturbing variable are obtained from a direct measurement of said perturbing variable.

7. The method according to claim 1 wherein said one or more other signals dependent on said perturbing variable are obtained from an indirect measurement of said perturbing variable.

8. The method according to claim 1 wherein said perturbing variable is temperature.

9. The method according to claim 1 wherein in step (v), said mathematical relationship is approximated by a linear relationship.

10. The method according to claim 1 wherein in step (v), said mathematical relationship fit to a mathematical function that is transformed to exhibit a linear dependence on said signal dependent on said perturbing variable.

11. The method according to claim 1 wherein said dose-response curves are fitted to any one of sigmoidal functions and polynomial functions.

12. The method according to claim 1 where said one or more assays is one assay, said suitable functional form is a sigmoid described by where S is the assay signal and C is the assay concentration and $a_1$, $a_2$, $a_3$ and $a_4$ are assay parameters, and a first of said one or more signals dependent on said perturbing variable is a direct measurement of $a_1$ via an assay reaction, and a second signal dependent on said perturbing variable is not a direct measurement of an assay parameter, and wherein:

i) said first signal dependent on said perturbing variable is used in step v) of claim 1 to provide a value of $a_2$; and ii) said second signal dependent on said perturbing variable is used in step v) of claim 1 to provide a value of $a_3$ and $a_4$; and iii) as a result of single assay parameters having been provided in step ii), no averaging is performed in step vi) of claim 1, whereby changes in additional perturbing variables that substantially affect $a_1$ and $a_2$ but not $a_3$ and $a_4$ are additionally compensated.

13. The method according to claim 1, wherein said one or more other signals dependent on said perturbing variable are produced by replicate measurements for the purpose of obtaining a compensated dose-response curve for each of said one or more assays with improved precision.

14. The method according to claim 13 wherein an outlier test is performed on said replicate measurements as a quality control means to determine a validity of said compensated dose-response curve for each of said one or more assays.

15. The method according to claim 1 wherein in addition to when performing one or more assays of unknown samples, one or more known standards for said one or more assays are also assayed as controls to determine a validity of said compensated dose-response curve for at least one of said one or more assays by the steps of:

a) performing one of said one or more assays to measure an assay signal from a known standard;

b) substituting said assay signal from said known standard into said compensated dose-response curve for said one of said one or more assays to obtain a predicted concentration of said known standard;

c) comparing said predicted concentration of said known standard with a known concentration of said known standard and determining whether or not said comparison passes a predetermined quality control criterion;

d) repeating steps a) through c) until each one of said one or more known standards for said one or more assays has been measured and tested; and e) provided that each of said comparisons pass said predetermined quality control criteria, concluding that said compensated dose-response curve for each of said one or more assays is valid.

16. The method according to claim 1 wherein said one or more other signals dependent on said perturbing variable are assay signals at known concentrations obtained for one of said one or more assays, whereby said re-measured other signals dependent on said perturbing variable are obtained by performing said one of said one or more assays with known standards at said known concentrations, and wherein during said step of characterizing a dependence of said dose-response curve of one or more assays on said perturbing variable, said other signals dependent on said perturbing variable are obtained, at each of said different values of said perturbing variable, from any one of the following two steps:

1) performing said one of said one or more assays with known standards at said known concentrations; and 2) indirectly obtaining assay signals at known concentrations by fitting said assay signals measured from said set of known standards for said one of said one or more assays to a suitable functional form, thereby obtaining a dose-response curve, and substituting said known concentrations into said dose-response curve and solving for said assay signals;

and wherein said one or more other signals dependent on said perturbing variable measured with said periodically measured dose-response curve for said one or more assays are obtained by any one of the following two steps:

1) measuring known standards at said known concentrations with said periodically measured dose-response curve; and 2) indirectly obtaining assay signals at known concentrations by substituting said known concentrations into said periodically measured dose-response curve and solving for said assay signals.

17. The method according to claim 16 wherein said one or more assay signals from known standards for one of said one or more assays are assay signals produced by replicate measurements of a single standard for the purpose of obtaining a compensated dose-response curve for each of said one or more assays with improved precision.

18. The method according to claim 17 wherein an outlier test is performed on said assay signals produced by replicate measurements of a single standard as a quality control means to determine a validity of said compensated dose-response curve for each of said one or more assays.

19. The method according to claim 16 wherein said one or more assay signals from known standards for one of said one or more assays are assay signals measured for several different standards for the purpose of obtaining a compensated dose-response curve for each of said one or more assays with improved precision.

20. The method according to claim 16 wherein each one of said one or more assay signals from known standards for one of said one or more assays are employed as controls to verify the accuracy of said compensated dose-response curve for each of said one or more assays by the steps of:

a) obtaining updated assay parameters of said one of said one or more assays by adding to each assay parameter obtained from said previously measured dose response curve for said one of said one or more assays a value equal to the difference between an assay parameter calculated by said mathematical relationship by substituting one of said one or more signals from known standards re-measured with said assays for said unknown samples, and an assay parameter calculated by said mathematical relationship by substituting one of said one or more signals from said standards measured with said previously measured dose-response curve;

b) producing an updated dose-response curve from said updated assay parameters;

c) substituting each concentration of each of said known standards into said updated dose-response curve to obtain predicted signals for each of said known standards;

d) comparing said predicted signals with said re-measured signals and determining whether or not said comparisons pass predetermined quality control criteria;

e) repeating steps a) through d) for each of said known standards; and f) provided that each of said comparisons pass said predetermined quality control criteria, concluding that said compensated dose-response curve for each of said one or more assays is valid.

21. The method according to claim 20 wherein said known standards for one of said one or more assays include one standard with a concentration above a cutoff for said assay, and one standard with a concentration below a cutoff for said assay.

22. The method according to claim 16 wherein each one of said one or more assay signals from known standards for one of said one or more assays are employed to directly solve for an assay parameter of said one of said one or more assays, by the steps of:

a) selecting one of said one or more assay signals from known standards and one of said one or more assay parameters from said one of said one or more assays;

b) substituting said one of said one or more assay signals from known standards and a concentration corresponding to said one of said one or more signals into said compensated dose-response curve of said one of said one or more assays and solving for a new value of said one of said one or more assay parameters from said one of said one or more assays; and c) repeating the above two steps for each of said one or more assay signals;

wherein said compensated dose-response curve of said one of said one or more assays is regenerated using said new values of said one or more assay parameters.

23. The method according to claim 22 wherein one of said assay parameters is a factor multiplying a concentration in said dose-response curve of said one of said one or more assays.

24. The method according to claim 22 wherein one of said known standards has an analyte concentration substantially equal to that of a cutoff concentration of said one of said one or more assays.

25. The method according to claim 22 wherein additional quality control is achieved by comparing each of said new values of said assay parameters with each of said averaged values of said assay parameters and determining whether or not said comparisons pass predetermined quality control criteria, and wherein a conclusion is made that said compensated dose-response curve for each of said one or more assays is valid provided that each of said comparisons pass said quality control criteria.

26. The method according to claim 20 wherein each one of said one or more assay signals from known standards for one of said one or more assays are employed to directly solve for an assay parameter of said one of said one or more assays, by the steps of:
   a) selecting one of said one or more assay signals from known standards and one of said one or more assay parameters from said one of said one or more assays;
   b) substituting said one of said one or more assay signals from known standards and a concentration corresponding to said one of said one or more signals into said compensated dose-response curve of said one of said one or more assays and solving for a new value of said one of said one or more assay parameters from said one of said one or more assays; and
   c) repeating the above two steps for each of said one or more assay signals;
   wherein said compensated dose-response curve of said one of said one or more assays is regenerated using said new values of said one or more assay parameters.

27. The method according to claim 26 wherein one of said assay parameters is a factor multiplying a concentration in said dose-response curve of said one of said one or more assays.

28. The method according to claim 26 wherein one of said known standards has an analyte concentration substantially equal to that of a cutoff concentration of said one of said one or more assays.

* * * * *